US005958722A

United States Patent [19]
Kohnert et al.

[11] Patent Number: 5,958,722
[45] Date of Patent: *Sep. 28, 1999

[54] **USE OF RECOMBINANT INHIBITOR FROM *ERYTHRINA CAFFRA* FOR PURIFYING SERINE PROTEASES**

[75] Inventors: Ulrich Kohnert, Habach; Anne Stern, Penzberg; Stephan Fischer, Polling, all of Germany

[73] Assignee: Boehringer Mannheim GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/702,703

[22] PCT Filed: Mar. 13, 1995

[86] PCT No.: PCT/EP95/00926

§ 371 Date: Sep. 13, 1996

§ 102(e) Date: Sep. 13, 1996

[87] PCT Pub. No.: WO95/25168

PCT Pub. Date: Sep. 21, 1995

[30] Foreign Application Priority Data

Mar. 16, 1994 [DE] Germany .............................. 44 08 939
Jul. 8, 1994 [DE] Germany .............................. 44 24 171

[51] Int. Cl.$^6$ .............................. C12P 21/06; C12N 9/50; C07K 14/415; C07H 21/04
[52] U.S. Cl. ..................... 435/69.1; 435/212; 435/219; 435/226; 435/252.3; 435/252.33; 435/814; 435/815; 530/350; 536/23.1; 536/23.6
[58] Field of Search ..................... 435/226, 212, 435/219, 815, 814, 252.3, 252.33, 69.1; 536/23.1, 23.6; 530/350

[56] References Cited

U.S. PATENT DOCUMENTS 4,902,623 2/1990 Dowdle .................................. 435/226

FOREIGN PATENT DOCUMENTS 0 218 479 4/1987 European Pat. Off. .

OTHER PUBLICATIONS

Joubert et al. "The primary structure of the inhibitor of tissue plasminogen activator . . . " Thrombosis and Haemostasis 57(3), 356–360, Jun. 3, 1987.

Kouzuma, Y., "Isolation and primary structure of proteinase inhibitors from *Erythrina variegata* (Linn.) var. Orientalis seeds", Chemical Abstracts, vol. 119, No. 11, Abstract No. 111939, p. 397 (Sep. 13, 1993).

Kouzuma, Y., "Isolation and primary structure of proteinase inhibitors from *Erythrina variegata* (Linn.) var. Orientalis seeds", Biosci. Biotechnol. Biochem., vol. 56, No. 11, pp. 1819–1824 (1992).

Porath, J., and Olin, B., "Immobilized metal ion affinity adsorption and immobilized metal ion affinity chromatography of biomaterials", Biochemistry, vol. 22, pp. 1621–1630 (1983).

Teixeira, A., "Synthesis and expression of a gene coding for *Erythrina trypsin* inhibitor (ETI)", Biochimica Biophysica Acta, vol. 1217, No. 1, pp. 16–22 (1994).

*Primary Examiner*—Robert A. Wax
*Assistant Examiner*—Nashaat T. Nashed
*Attorney, Agent, or Firm*—Nikaido Marmelstein Murray & Oram, LLP

[57] ABSTRACT

Process for purifying serine proteases from a protein mixture by binding the serine protease to an immobilized polypeptide with the activity of an inhibitor DE-3 from *Erythrina caffra*, removing unbound components from the protein mixture, detaching the serine protease from the inhibitor and separating the immobilized inhibitor from the soluble serine protease and isolating serine protease which is characterized in that a polypeptide is used as the polypeptide which is the product of a prokaryotic or eukaryotic expression of an exogenous nucleic acid. This inhibitor is distinguished by an improved specific activity and is particularly suitable for the purification of plasminogen activators such as tissue plasminogen activators (t-PA and derivatives).

8 Claims, No Drawings

USE OF RECOMBINANT INHIBITOR FROM ERYTHRINA CAFFRA FOR PURIFYING SERINE PROTEASES

This is a U.S. national stage application of PCT/EP95/00926 filed on March 13, 1995.

The invention concerns an improved process for purifying serine proteases using a recombinant inhibitor DE-3 from *Erythrina caffra*. Immobilized trypsin inhibitors from Erythrina (ETI) are effective reagents for the affinity chromatographic purification of serine proteases and in particular of plasminogen activators (C. Heussen, J. Biol. Chem. 259 (1984) 11635–11638), β-trypsin, α-chymotrypsin and thrombin (S. Onesti et al., J. Mol. Recogn. 5 (1992) 105–114). These trypsin inhibitors have been known for a long time (C. Heussen, Haemostasis 11 (1982) P47 (Supplement); F. J. Joubert, Phytochemistry 21 (1982) 1213–1217; F. J. Joubert, Int. J. Biochem. 14 (1982) 187–193).

The inhibitor DE-3 from *E. caffra* is particularly suitable for the purification of plasminogen activators (F. J. Joubert in Thrombosis and Haemostasis 57 (1987) 356–360). The complete amino acid sequence of this inhibitor is also described in this publication. DE-3 can be isolated and purified from the seeds of *E. caffra* (F. J. Joubert, Int. J. Biochem. 14 (1982) 187–193).

A recombinant ETI is described by Teixeira et al., Biochimica et Biophysica Acta 1217 (1994) 16–22, whose specific inhibitory activity for tissue plasminogen activator is $1.7 \times 10^9$ U/mmol. In contrast the specific inhibitory activity of natural ETI is $1.94 \times 10^9$ U/mmol.

A similar situation applies to the inhibitory activity towards trypsin ($2.63 \times 10^{12}/3.21 \times 10^{12}$). Thus the specific inhibitory activity towards trypsin and tissue plasminogen activator of recombinant ETI prepared according to Teixeira is 20% less than the activity of natural ETI.

Recombinant ETI is obtained by expression according to Teixeira and purified by ammonium sulfate precipitation (80% saturation), dialysis against water and a cyanogen bromide cleavage in which the N-terminal sequence including the methionine is cleaved off. It is subsequently chromatographed on an affinity chromatography column (Sephadex G50).

The object of the invention is to improve the effectiveness of processes for the purification of serine proteases using ETI.

The invention concerns a process for the purification of serine proteases from a protein mixture by binding the serine protease to an immobilized polypeptide which has the activity of an inhibitor DE-3 from *Erythrina caffra*, removing the unbound components from the protein mixture, detaching the serine protease from the inhibitor, separating the immobilized inhibitor from the soluble serine protease and isolating the serine protease which is characterized in that a polypeptide is used as the polypeptide which is the product of a prokaryotic or eukaryotic expression of an exogenous nucleic acid (preferably DNA) and is purified chromatographically by means of an anion exchanger, cation exchanger or a nickel chelate column. surprisingly it was found that the recombinant polypeptide produced according to the invention which has the activity of an inhibitor DE-3 from Erythrina caffra has a substantially increased specific affinity towards serine proteases compared to inhibitor DE-3 from *E. caffra* isolated from natural sources.

The "activity" of an inhibitor DE-3 from *E. caffra* is essentially to be understood as its specific inhibitory activity towards serine proteases in particular to tissue plasminogen activators. In this case the specific inhibitory activity of the inhibitor is at 1.07 U/mg or more with regard to trypsin. The inhibition is achieved by binding between inhibitor and serine protease.

The process according to the invention is particularly advantageous for purifying plasminogen activators such as tissue plasminogen activators (t-PA) and derivatives (e.g. mutations and deletions) thereof. t-PA and derivatives are described for example in EP-B 0 093 619, U.S. Pat. No. 5,223,256, WO 90/09437 and T. J. R. Harris, Protein Engineering 1 (1987) 449–458.

The production of recombinant inhibitors can be carried out according to methods familiar to a person skilled in the art.

For this a nucleic acid (preferably DNA) is firstly prepared which is able to produce a protein which possesses the activity of the inhibitor DE-3. The DNA is cloned into a vector that can be transferred into a host cell and can be replicated there. Such a vector contains operator elements in addition to the inhibitor sequence which are necessary for the expression of the DNA. This vector which contains the inhibitor DNA and the operator elements is transferred into a vector that is able to express the DNA of the inhibitor. The host cell is cultured under conditions that allow the expression of the inhibitor. The inhibitor is isolated from these cells. During this process suitable measures are undertaken to ensure that the activator can assume an active tertiary structure in which it exhibits inhibitor properties.

In this connection it is not necessary that the inhibitor has the exact amino acid sequence corresponding to SEQ ID NO: 2. Inhibitors are also suitable which have essentially the same sequence and which are polypeptides with the activity (capability of binding to serine proteases, in particular to t-PA) of an inhibitor DE-3 from *Erythrina caffra*. It has turned out that homology of the amino acid sequence of 80% is advantageous, preferably of 90%. However, the amino acid sequence SEQ ID NO:2 is preferably used which in the case of expression in prokaryotic host cells, but not after eukaryotic expression, contains a N-terminal methionine.

The invention in addition concerns a nucleic acid which is essentially identical to the nucleotides 9 to 527 of SEQ ID NO: 1 and codes for a polypeptide with the activity of an inhibitor DE-3 from *Erythrina caffra*, or a nucleic acid which codes for the same polypeptide within the scope of the degeneracy of the genetic code. A DNA is preferred and in particular a DNA of the sequence 9 to 527 of SEQ ID NO: 1. For the expression in eukaryotic or prokaryotic host cells, the nucleic acid contains at its 5' end the eukaryotic or prokaryotic transcription and translation signals which are familiar to a person skilled in the art.

The nucleic acid sequence of the inhibitor is preferably identical to the nucleotides 9 to 527 of SEQ ID NO:1. However, modifications may be made in order to facilitate the production of the vectors or to optimize expression. Such modifications are for example:

Modification of the nucleic acid in order to introduce various recognition sequences of restriction enzymes in order to facilitate ligation, cloning and mutagenesis steps Modification of the nucleic acid in order to incorporate preferred codons for the host cell Extension of the nucleic acid by additional operator elements in order to optimize expression in the host cell.

The inhibitor is preferably expressed in microorganisms such as *E. coli*. It is, however, also possible to carry out the expression in eukaryotic cells such as yeast, CHO cells or insect cells.

For this, biological functional plasmids or viral DNA vectors are used which essentially contain the nucleotides 9 to 527 of SEQ ID NO:1 or a nucleic acid which codes for the same polypeptide within the scope of the degeneracy of the genetic code. Prokaryotic or eukaryotic host cells are stably transformed or transfected with such vectors.

The expression vectors must contain a promoter that allows the expression of the inhibitor protein in the host organism. Such promoters are known to a person skilled in the art and are for example the lac promoter (Chang et al., Nature 198 (1977) 1056), trp (Goeddel et al., Nuc. Acids Res. 8 (1980) 4057), $\lambda$PL promoter (Shimatake et al., Nature 292 (1981) 128) and T5 promoter (U.S. Pat. No. 4,689,406). Synthetic promoters such as for example the tac promoter (U.S. Pat. No. 4,551,433) are also suitable. Coupled promoter systems such as for example the T7 RNA polymerase/promoter system (Studier et al., J. Mol. Biol. 189 (1986) 113) are also suitable. Hybrid promoters from a bacteriophage promoter and the operator region of the microorganism (EP-A 0 267 851) are also suitable. In addition to the promoter it is also necessary to have an effective ribosome binding site. In the case of *E. coli* this ribosome binding site is denoted Shine-Dalgarno (SD) sequence (Shine et al., Nature (1975) 25434; J. Sambrook et al., "Expression of cloned genes in *E. coli*" in Molecular Cloning: A laboratory manual (1989) Cold Spring Harbor Laboratory Press, USA).

In order to improve the expression it is possible to express the inhibitor protein as a fusion protein. In this case a DNA which codes for the N-terminal part of an endogenous bacterial protein or another stable protein is usually fused to the 5' end of the sequence coding for the inhibitor protein. Examples of this are lacZ, trpE.

After expression the fusion proteins are preferably cleaved with enzymes (e.g. factor Xa) (Nagai et al., Nature 309 (1984) 810). Further examples of cleavage sites are the IgA protease cleavage site (WO 91/11520) and the ubiquitin cleavage site (Miller et al., Bio/Technology 7 (1989) 698).

The recombinant protein that is firstly obtained as inactive inclusion bodies can be converted into a soluble active protein by methods familiar to a person skilled in the art. For this the inclusion bodies are for example solubilized with guanidine hydrochloride or urea in the presence of a reducing agent, reduced, the reducing agent is removed e.g. by dialysis and preferably renatured using a redox system such as reduced and oxidized glutathione.

Such methods are described for example in U.S. Pat. No. 4,933,434, EP-B 0 241 022 and EP-A 0 219 874.

It is also possible to secrete the proteins from the microorganism as active proteins. For this a fusion protein is preferably used which is composed of the signal sequence that is suitable for the secretion of proteins in the host organisms used (U.S. Pat. No. 4,336,336) and the nucleic acid which codes for the inhibitor protein. In this case the protein is either secreted into the medium (in the case of gram-positive bacteria) or into the periplasmatic space (in the case of gram-negative bacteria). It is expedient to introduce a cleavage site between the signal sequence and the sequence coding for the inhibitor which enables the cleavage of the inhibitor protein either during processing or in an additional step. Such signal sequences are for example ompA (Ghrayeb et al., EMBO J. 3 (1984) 2437) and phoA (Oka et al., Proc. Natl. Acad. Sci. USA 82 (1985) 7212).

The vectors in addition contain terminators. Terminators are DNA sequences that signal the end of a transcription process. They are usually characterized by two structural features: a reversed repetitive G/C-rich region which can intramolecularly form a double helix and a number of U (or T) residues. Examples are the trp attenuator and terminator in the DNA of the phage fd and rrnB (Brosius et al., J. Mol. Biol. 148 (1981) 107–127).

In addition the expression vectors usually contain a selectable marker in order to select transformed cells. Such selectable markers are for example the resistance genes for ampicillin, chloramphenicol, erythromycin, kanamycin, neomycin and tetracyclin (Davies et al., Ann. Rev. Microbiol. 32 (1978) 469). Selectable markers which are also suitable are the genes for substances essential for the biosynthesis of substances necessary for the cell such as e.g. histidine, thryptophan and leucine.

Numerous suitable bacterial vectors are known. For example vectors have been described for the following bacteria: Bacillus subtilis (Palva et al., Proc. Natl. Acad. Sci. USA 79 (1982) 5582), *E. coli* (Aman et al., Gene 40 (1985) 183; Studier et al., J. Mol. Biol. 189 (1986) 113), Streptococcus cremoris (Powell et al., Appl. Environ. Microbiol. 54 (1988) 655), *Streptococcus lividans* and *Streptomyces lividans* (U.S. Pat. No. 4,747,056).

In addition to prokaryotic microorganisms, it is also possible to express inhibitor proteins in eukaryotes (such as for example CHO cells, yeast or insect cells). Yeast and insect cells are preferred as the eukaryotic expression system. The expression in yeast can be achieved by three types of yeast vectors (integrating YIp (yeast integrating plasmids) vectors, replicating YRp (yeast replicon plasmids) vectors and episomal YEp (yeast episomal plasmids) vectors). Further details of these are described for example in S. M. Kingsman et al., Tibtech 5 (1987) 53–57.

Further genetic engineering methods for the production and expression of suitable vectors are described in J. Sambrook et al., "Expression of cloned genes in *E. coli*" in Molecular cloning: A laboratory manual (1989) Cold Spring Harbor Laboratory Press, USA).

After production, the recombinant ETI is purified chromatographically by means of an anion exchanger such as a Q-Sepharose® column, a cation exchanger (e.g. based on sulfopropyl) or by means of a nickel chelate column as described for example in Porath, J. & Olin, B., Biochemistry 22 (1983), 1621–1630. surprisingly after this purification procedure a recombinant ETI is obtained whose inhibitory activity towards serine proteases such as trypsin and tissue plasminogen activator is substantially higher than the inhibitory activity of natural ETI.

A polypeptide prepared and purified in this manner has the activity of a DE-3 inhibitor from *Erythrina caffra* and is obtainable by culturing prokaryotic or eukaryotic host cells which are transformed or transfected with an exogenous nucleic acid (preferably DNA) which essentially corresponds to the sequence of nucleotides 9 to 527 of SEQ ID NO: 1 or to a nucleic acid which codes for the same polypeptide within the scope of the degeneracy of the genetic code, in a manner that enables the host cells to express the polypeptide under suitable nutrient conditions and isolating the desired polypeptide which has a specific inhibitory activity of ca. 1.07 U/mg or more (preferably 1.07 to 1.8 U/mg) towards trypsin. In various lots of the recombinant ETI a specific activity of for example 1.2, 1.5 and 1.6 U/mg was found. This activity is obtained after chromatographic purification on an anion exchanger, cation exchanger or on a nickel chelate column.

The invention in addition concerns a process for the production of a recombinant polypeptide which has the activity of a DE-3 inhibitor from *Erythrina caffra* (ETI) by culturing prokaryotic or eukaryotic host cells which are transformed or transfected with an exogenous nucleic acid (preferably DNA) which essentially corresponds to the sequence of nucleotides 9 to 527 of SEQ ID NO: 1 or to a nucleic acid which codes for the same polypeptide within the scope of the degeneracy of the genetic code, in a manner that enables the host cells to express the polypeptide under suitable nutrient conditions, isolating the polypeptide from the host cells and chromatographic purification on an anion exchanger, cation exchanger or on a nickel chelate column.

The purification of serine proteases using recombinant ETI is carried out according to methods familiar to a person skilled in the art (cf. e.g. F. J. Joubert (1987)). For this ETI is bound covalently to a matrix (e.g. CNBr-Sepharose colum) and the protein mixture which contains the serine protease is applied to the column under neutral or weakly alkaline conditions and a chromatography is carried out. The elution is achieved by lowering the pH to < pH 5.5 or by using buffer solutions that contain chaotropic agents such as e.g. KSCN. The eluate has a protein purity of over 95% with regard to the serine protease. For further use it is expedient to transfer the serine protease into the buffer solution that is desired in each case by dialysis.

The immobilization of the inhibitor and all further steps in the procedure for the purification of serine protease and t-PA can be carried out in an analogous manner to that for the inhibitor DE-3 isolated from *E. caffra*. Such processes are for example described in EP-B 0 218 479, EP-B 0 112 122, U.S. Pat. No. 4,902,623. It is expedient to carry out the immobilization on an inert carrier, preferably on CNBr-Sepharose®.

The invention is described in more detail by the following examples and sequence protocols.

EXAMPLE 1

Expression of ETI in *E. coli* a) Gene synthesis

A corresponding nucleic acid sequence was derived from the amino acid sequence of ETI from *Erythrina caffra* (Joubert and Dowdle, Thrombosis and Haemostasis 57 (3) (1987) 356–360) using the codons preferred by *E. coli* and prepared synthetically according to the method by Beattie and Fowler (Nature 352 (1991) 548–549). In order to facilitate the cloning, a cleavage site for the restriction enzyme EcoRI was inserted at the 5' end and a cleavage site for the restriction enzyme HindIII was inserted at the 3' end. The synthesized nucleic acid was recleaved with the enzymes EcoRI and HindIII and ligated with the cloning vector pBS+ (Stratagene, US, Catalogue No 211201, derivative of the fl phage and Stratagene's pBS plasmid with the T3 and T7 promoter gene, ampicillin resistance gene, fl origin, ColE-1 origin, lacd gene, lacZ gene and a multiple cloning site) which previously had also been digested with EcoRI and HindIII. The ligation preparation was transformed into *Escherichia coli*. The clones obtained, selected on ampicillin, were analysed by restriction with the enzymes EcoRI and HindIII. The resulting clone, pBS+ETI, contains an additional EcoRI/HindIII fragment with a size of 539 bp and has SEQ ID NO: 1.

b) Expression vector

Plasmid pBS+ETI was recleaved with the restriction enzymes EcoRI and HindIII and the 539 bp large fragment was isolated. The expression vector pBTacl (from Boehringer Mannheim GmbH, Catalogue No. 1081365, based on pUC8, H. Haymerle et al., Nucl. Acid Res. 14 (1986) 8615–8624) was likewise digested with the enzymes EcoRI and HindIII and the 4.6 kb large vector fragment was isolated. Both fragments were ligated and transformed together into *E. coli* (DSM 5443) together with the helper plasmid pUBS520 (Brinkmann et al., Gene 85 (1989) 109–114) which contains the lac repressor gene. The clones were selected on the basis of the ampicillin and kanamycin resistance mediated by the plasmids. Plasmid pBTETI obtained contains an additional EcoRI/HindIII fragment having a size of 539 bp compared to the starting vector pBTac1.

DSM 3689 which already contains an $I^q$ plasmid can be used in an analogous manner instead of DSM 5443. In this case the helper plasmid pUB520 is not necessary.

c) Expression of recombinant ETI (recETI) in *E. coli*

In order to check the expression rate, the *E. coli* strain DSM 5443 was cultured with plasmids PBTETI and pUBS520 in LB medium (Sambrook et al., Molecular Cloning (1989) Cold Spring Harbor) in the presence of ampicillin and kanamycin (50 µg/ml final concentration in each case) to an optical density (OD) of 0.6 at 550 nm. The expression was initiated by addition of 5 mM IPTG. The culture was incubated for a further 4 hours. Subsequently the *E. coli* were collected by centrifugation and resuspended in buffer (50 mM Tris-HCl pH 8, 50 mM EDTA); lysis of *E. coli* was achieved by sonification. The insoluble protein fractions (inclusion bodies) were collected by renewed centrifugation and resuspended in the above-mentioned buffer by sonification. The suspension was admixed with ¼ volumes application buffer (250 mM Tris-HCl pH 6.8, 0.01 M EDTA, 5% SDS, 5% mercaptoethanol, 50% glycerol and 0.005% bromophenol blue) and analysed with the aid of a 12.5% SDS polyacrylamide gel. As a control the same preparation was carried out with a culture of *E. coli* (pBTETI/pUBS520) which had not been admixed with IPTG and applied to the polyacrylamide gel. A clear band with a molecular weight of about 22 kD can be seen in the preparation of the IPTG-induced culture after staining the gel with 0.2% Coomassie blue R250 (dissolved in 30% methanol and 10% acetic acid) and destaining the gel in a methanol-acetic acid mixture.

This band cannot be found in the preparation of the non-induced *E. coli* cells.

EXAMPLE 2

Renaturation and purification of recETI 50 g inclusion bodies (IBs) were solubilized with 0.1 M Tris/HCl, pH 8.5, 6 M guanidine, 0.1 M DTE, 1 mM EDTA (90 min at 25° C., $C_{prot.}$=10 mg/ml) and, after adjusting the pH value to 2.5 (HCl), dialysed against 3 mol/l guanidine/HCl. The dialysate was centrifuged (SS34, 13,000 rpm) and adjusted to $C_{prot.}$=36.9 mg/ml by concentration over YM 10. A 1 l reaction vessel was filled with 0.1 M Tris/HCl, pH 8.5, 1 mM EDTA, 1 mM GSH, 0.1 mM GSSG. The renaturation was carried out at 20° C. by a 16-fold addition of the dialysate (600 µg protein/ml buffer each time) at intervals of 30 min.

The renaturation yields 2.8 U/ml active ETI.

Purification of recETI a) by means of an anion exchanger

RecETI is renatured in 0.1 M Tris/HCl, pH 8.5, 1 mM EDTA, 1 mM GSH, 0.1 mM GSSG. The renaturate is diluted 1:2 with $H_2$, adjusted to pH 8.0 with HCl, dialysed against 50 mM Tris/HCl pH 8.0 and applied to a Q-Sepharose® column equilibrated with 50 mM Tris/HCl, pH 8.0 (5 mg protein/ml gel). After washing the column with equilibration buffer and with 50 mM $Na_2HPO_4/H_3PO4$, pH 8.0 (five column volumes each time), elution is achieved with 50 mM $Na_2HPO_4/H_3PO_4$, pH 8.0, 0.2 M NaCl.

b) by means of a cation exchanger

Renatured ETI was adjusted to pH 4.0 by addition of HCl and dialysed against 50 mM NaOAc/HCl, pH 4.0 (Cross Flow). The dialysate was centrifuged (13,000 rpm, 30 min, SS 34) and applied to a TSK-SP column (cation exchanger with sulfopropyl side groups, Merck, Germany, volume 15 ml) that had been equilibrated with 50 mM NaOAc/HCl, pH 4.0. After washing the column with the equilibration buffer and with 50 mM NaOAc/HCl, pH 4.0, 0.1 M NaCl, it is eluted with 50 mM NaOAc/HCl, pH 4.0, 0.2 M NaCl.

The purity of the eluate was examined by SDS-PAGE and by means of RP-HPLC.

RESULT

ETI binds to the TSK-SP column under the conditions used and can be eluted with 0.2 M NaCl. SDS-PAGE and RP-HPLC analysis result in a purity of >95%.

EXAMPLE 3

Comparison of the Specific Activity of recETI and of ETI From Seeds of *Erythrina Caffra*

RecETI and ETI isolated from the seeds of *E. caffra* were dialysed against 50 mM $Na_2HPO_4/H_3PO_4$, pH 8.0, 0.2 M NaCl and adjusted to a protein concentration of 0.8 mg/ml. The protein concentration was determined by measuring the UV absorbance at 280 nm ($\epsilon$=1.46 cm$^2$/mg).

Determination of the ETI Activity

The inhibition of trypsin by ETI is measured using N-α-benzoylethyl ester (BAEE) as the substrate. 40 μl trypsin solution (0.13 mg/ml 2 mM HCl) is mixed with 60 μl test buffer (0.1 M Tris/HCl, pH 8.0) and 100 μl ETI solution in a quartz cuvette and incubated for 5 min at 30° C. After addition of 800 μl BAEE solution (20 mg BAEE× HCl/100 ml test buffer) the increase in absorbance/min is determined at 253 nm.

The ETI activity is determined according to the following formula:

$$U/ml = [1 - A_{sample}/A_{trypoin}] \cdot C_{trypoin} \cdot 0.328 \cdot V$$

$A_{sample}$: increase in absorbance/min of inhibited sample
$A_{trypsin}$: increase in absorbance/min of uninhibited trypsin
$C_{trypoin}$: trypsin concentration in the test mixture
V: (factor of dilution) predilution of the ETI solution 7 (factor of dilution)

| Protein | $C_{prot.}$ (protein concentration) (mg/ml) | Activity (U/ml) | Spec. activity (U/mg) |
|---|---|---|---|
| ETI (seeds) | 0.81 | 0.71 | 0.88 |
| recETI | 0.83 | 0.89 | 1.07 |

Result: The specific activity of recETI is 20% higher than the specific activity of ETI isolated by classical methods from the seeds of *E. caffra*.

In further lots of recombinant ETI 1.2, 1.5 and 1.6 U/mg were for example found as the specific activity.

EXAMPLE 4

Coupling recETI to CNBr-8epharoses®

170 mg purified recETI was dialysed against 0.05 M $H_3BO_3$/NaOH, pH 8.0, 0.5 M NaCl (coupling buffer) and mixed with 7.5 g CNBr-Sepharose® (swollen overnight in 500 ml 1 mM HCl, then aspirated and suspended in coupling buffer). The suspension was incubated for 90 min at room temperature, aspirated and shaken overnight with 400 ml 0.1 M Tris/HCl, pH 8.0. The recETI-Sepharose® was aspirated and equilibrated with 0.7 M arginine/$H_3PO_4$, pH 7.5.

EXAMPLE 5

Purification of a Recombinant Plasminogen Activator 54 mg recombinant plasminogen activator K2P (prepared according to WO 90/09437 or U.S. Pat. No. 5,223,256) was applied to a recETI-Sepharose column equilibrated with 0.7 M arginine/$H_3PO_4$, pH 7.5. After washing with equilibration buffer and with 0.3 M arginine/$H_3PO_4$, pH 7.0 (five column volumes each time), it was eluted with 0.3 M arginine/$H_3PO_4$, pH 4.5. The plasminogen activator content in the eluate was determined using S 2288 as the substrate (Kohnert et al., Prot. Engineer. 5 (1992) 93–100).

Result: The binding capacity of the recETI-Sepharose for asminogen activator is 1.2 mg (corresponding to 0.63 MU) asminogen activator/ml recETI-Sepharose.

We claim:

1. A process for isolating a plasminogen activator from a protein mixture, comprising the steps of:
   expressing, in a prokaryotic or eukaryotic cell, an exogenous nucleic acid which encodes a polypeptide which has the same specific inhibitory activity for tissue plasminopen activator as a tissue plasminogen activator inhibitor DE-3 from *Erythrina caffra*,
   chromatographically purifying said polypeptide by means of an anion exchanger, cation exchanger or by means of a nickel chelate,
   immobilizing said polypeptide,
   binding a plasminogen activator contained in a protein mixture to said immobilized polypeptide,
   separating unbound components from the immobilized polypeptide,
   removing the plasminogen activator from the immobilized polypeptide, and
   recovering the isolated plasminogen activator, wherein said polypeptide has an amino acid sequence according to SEQ ID NO:2.

2. The process according to claim 1, wherein said polypeptide is immobilized on an inert carrier.

3. A process for the production of a polypepuide which has the same specific inhibitory activity for tissue plasminogen activator as a tissue plasminogen activator inhibitor DE-3 from *Erythrina caffra*, comprising the steps of:
   transforming or transfecting prokaryotic or eukaryotic host cells with an exogenous nucleic acid which encodes a polypeptide with the amino acid sequence of SEQ ID NO:2,
   culturing said host cells under conditions which result in the expression of said polypeptide,
   chromatographically purifying said polypeptide by means of an anion exchanger, cation exchanger or by means of a nickel chelate, and
   isolating said polypeptide, wherein said polypeptide has a specific inhibitory activity towards trypsin of 1.07 U/mg and wherein said polypeptide has an amino acid sequence according to SEQ ID NO: 2.

4. The process according to claim 3, wherein said exogenous nucleic acid corresponds to nucleotides 9 to 527 of SEQ ID NO:1.

5. The process according to claim 3, wherein said polypeptide is isolated by chromatographic purification on an anion exchanger, cation exchanger or on a nickel chelate column.

6. An isolated and purified polypeptide, wherein said polypeptide is obtainable by a process comprising the steps of:
   transforming or transfecting prokaryotic or eukaryotic host cells with an exogenous nucleic acid which encodes a polypeptide according to SEQ ID NO:2,
   culturing said host cells under conditions which result in the expression of said polypeptide,
   chromatographically purifying said polypeptide by means of an anion exchanger, cation exchanger or by means of a nickel chelate, and
   isolating said polypeptide wherein said polypeptide has an amino acid sequence accordking to SEQ ID. NO:2.

7. A recombinant polypeptide according to claim 6, wherein said polypeptide has the same specific inhibitory activity for tissue plasminogen activator as a tissue plasminogen activator inhibitor DE-3 from *Erythrina caffra*, and wherein said polypeptide has a specific activity towards trypsin of 1.07 U/mg or more.

8. The polypeptide according to claim 6, wherein said exogenous nucleic acid corresponds to nucleotides 9 to 527 from SEQ ID NO: 1.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 539 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 9..527

(D) OTHER INFORMATION: /note= "Met only included in prokaryontic expression"

(ix) FEATURE:
(A) NAME/KEY: misc_feature
(B) LOCATION: 1..8
(D) OTHER INFORMATION: /function= "multiple cloning site"

(ix) FEATURE:
(A) NAME/KEY: misc_feature
(B) LOCATION: 528..539
(D) OTHER INFORMATION: /function= "multiple cloning site"

(xi) SEQUENCE DESCRIPTION: SEQ ID NO: 1:

```
GAATTCTT ATG GTA TTA TTA GAT GGT AAC GGC GAA GTG GTG CAG AAC GGC         50
         Met Val Leu Leu Asp Gly Asn Gly Glu Val Val Gln Asn Gly
         1               5                   10

GGT ACC TAT TAT CTG CTG CCG CAG GTG TGG GCG CAG GGC GGC GGC GTG         98
Gly Thr Tyr Tyr Leu Leu Pro Gln Val Trp Ala Gln Gly Gly Gly Val
15                  20                  25                  30

CAG CTG GCG AAA ACC GGC GAA GAA ACC TGC CCG CTG ACC GTG GTG CAG         146
Gln Leu Ala Lys Thr Gly Glu Glu Thr Cys Pro Leu Thr Val Val Gln
                35                  40                  45

AGC CCG AAC GAA CTG AGC GAT GGC AAA CCG ATT CGT ATT GAA AGC CGT         194
Ser Pro Asn Glu Leu Ser Asp Gly Lys Pro Ile Arg Ile Glu Ser Arg
        50                  55                  60

CTG CGT AGC GCG TTT ATT CCG GAT GAT GAT AAA GTG CGT ATT GGC TTT         242
Leu Arg Ser Ala Phe Ile Pro Asp Asp Asp Lys Val Arg Ile Gly Phe
            65                  70                  75

GCG TAT GCG CCG AAA TGC GCG CCG AGC CCG TGG TGG ACC GTG GTG GAA         290
Ala Tyr Ala Pro Lys Cys Ala Pro Ser Pro Trp Trp Thr Val Val Glu
80                  85                  90

GAT GAA CAG GAA GGC CTG AGC GTG AAA CTG AGC GAA GAT GAA AGC ACC         338
Asp Glu Gln Glu Gly Leu Ser Val Lys Leu Ser Glu Asp Glu Ser Thr
95                  100                 105                 110

CAG TTT GAT TAT CCG TTT AAA TTT GAA CAG GTG AGC GAT CAG CTG CAT         386
Gln Phe Asp Tyr Pro Phe Lys Phe Glu Gln Val Ser Asp Gln Leu His
                115                 120                 125

AGC TAT AAA CTG CTG TAT TGC GAA GGC AAA CAT GAA AAA TGC GCG AGC         434
Ser Tyr Lys Leu Leu Tyr Cys Glu Gly Lys His Glu Lys Cys Ala Ser
        130                 135                 140

ATT GGC ATT AAC CGT GAT CAG AAA GGC TAT CGT CGT CTG GTG GTG ACC         482
Ile Gly Ile Asn Arg Asp Gln Lys Gly Tyr Arg Arg Leu Val Val Thr
            145                 150                 155

GAA GAT TAT CCG CTG ACC GTG GTG CTG AAA AAA GAT GAA AGC AGC             527
Glu Asp Tyr Pro Leu Thr Val Val Leu Lys Lys Asp Glu Ser Ser
160                 165                 170

TGATAAAAGC TT                                                           539
```

(2) INFORMATION FOR SEQ ID NO: 2:

(i) SEQUENCE CHARACTERISTICS:
(A) LENGTH: 173 amino acids
(B) TYPE: amino acid
(D) TOPOLOGY: linear (ii) MOLECULE TYPE: protein (xi) SEQUENCE DESCRIPTION: SEQ ID NO: 2:

```
Met Val Leu Leu Asp Gly Asn Gly Glu Val Val Gln Asn Gly Gly Thr
1               5                   10                  15

Tyr Tyr Leu Leu Pro Gln Val Trp Ala Gln Gly Gly Gly Val Gln Leu
            20                  25                  30

Ala Lys Thr Gly Glu Glu Thr Cys Pro Leu Thr Val Val Gln Ser Pro
```

-continued

```
                35                   40                  45
Asn Glu Leu Ser Asp Gly Lys Pro Ile Arg Ile Glu Ser Arg Leu Arg
            50                  55                  60

Ser Ala Phe Ile Pro Asp Asp Lys Val Arg Ile Gly Phe Ala Tyr
 65                 70                  75                  80

Ala Pro Lys Cys Ala Pro Ser Pro Trp Trp Thr Val Val Glu Asp Glu
                85                  90                  95

Gln Glu Gly Leu Ser Val Lys Leu Ser Glu Asp Glu Ser Thr Gln Phe
               100                 105                 110

Asp Tyr Pro Phe Lys Phe Glu Gln Val Ser Asp Gln Leu His Ser Tyr
           115                 120                 125

Lys Leu Leu Tyr Cys Glu Gly Lys His Glu Lys Cys Ala Ser Ile Gly
           130                 135                 140

Ile Asn Arg Asp Gln Lys Gly Tyr Arg Arg Leu Val Val Thr Glu Asp
145                 150                 155                 160

Tyr Pro Leu Thr Val Val Leu Lys Lys Asp Glu Ser Ser
                165                 170
```